United States Patent
Hiramoto et al.

(10) Patent No.: US 6,838,103 B2
(45) Date of Patent: Jan. 4, 2005

(54) DETERIORATION PREVENTIVE AGENT FOR MILK-CONTAINING FOODS

(75) Inventors: Tadahiro Hiramoto, Kanagawa (JP); Kenji Saiki, Kanagawa (JP); Nobutada Kaneko, Kanagawa (JP); Yoshihiko Maruta, Kanagawa (JP); Kazumasa Sakamoto, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 262 days.

(21) Appl. No.: 10/096,832

(22) Filed: Mar. 14, 2002

(65) Prior Publication Data

US 2002/0197370 A1 Dec. 26, 2002

(30) Foreign Application Priority Data

Mar. 15, 2001 (JP) .................................. 2001-073712

(51) Int. Cl.⁷ ............................................... A23C 3/00
(52) U.S. Cl. .................. 426/330.2; 426/321; 426/330; 426/534; 426/580
(58) Field of Search ................................. 426/321, 330, 426/330.2, 534, 580, 581, 582, 583, 584, 585, 586, 587, 588, 590

(56) References Cited

U.S. PATENT DOCUMENTS 3,810,990 A    5/1974   Jurd et al.
4,201,639 A    5/1980   Light et al.
6,475,544 B1 * 11/2002  Hiramoto et al. ........... 426/321

FOREIGN PATENT DOCUMENTS

JP   61-15834 A    1/1986
JP   9-262069 A   10/1997
JP   2000-319154 A 11/2000

OTHER PUBLICATIONS

S. Arctander, *Perfume and Flavor Chemicals* (*Aroma Chemicals*) *I.*, published by the Author, Montclair, NJ: 1969, p. 704.
P.R. Ashurst, et al., *Food Flavorings*, 2$^{nd}$ Ed., Blackie Academic and Professional, London: 1995; pp. 209–210.
XP–002236649 (1997) Abstract.
XP–002236650 (1986) Abstract.
European Search Report dated Apr. 17, 2003.

* cited by examiner

Primary Examiner—Leslie Wong
(74) Attorney, Agent, or Firm—Sughrue Mion, PLLC

(57) ABSTRACT

Disclosed are a deterioration preventive agent for milk-containing foods containing as its active ingredient a coumarin analog represented by the general formula (1) below, a glycoside of that analog, or a plant extract containing the coumarin analog or its glycoside:

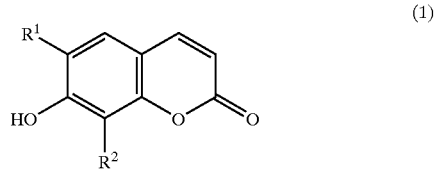

(1)

(wherein $R^1$ represents a hydrogen atom, a hydroxyl group or a methoxy group, $R^2$ represents a hydrogen atom or a hydroxyl group, and $R^1$ and $R^2$ are not both hydrogen atoms). The deterioration preventive agent according to the present invention demonstrates superior deterioration preventive effects for milk-containing foods. In addition, the deterioration preventive agent provided by the present invention is friendly to the environment and people.

15 Claims, No Drawings

DETERIORATION PREVENTIVE AGENT FOR MILK-CONTAINING FOODS

BACKGROUND OF THE INVENTION

1. Field of the Invention

The present invention relates to a deterioration preventive agent for various milk-containing foods. Namely, the present invention relates to a deterioration preventive agent for milk-containing foods having as its active ingredient a coumarin analog, its glycoside or a plant extract containing the coumarin analog or its glycoside. In addition, the present invention relates to a quality retention method for milk-containing foods.

2. Description of the Related Art

Milk-containing foods are typically susceptible to the effects of light, heat, air and so forth during the manufacturing process, distribution stage and each stage of storage, causing them to lose their inherent flavor and aroma and generate a peculiar foul odor due to deterioration of internal ingredients with the passage of time, and making them susceptible to the problem of the generation of a peculiar foul odor caused by what is called deterioration of the raw material. Thus, milk-containing foods lose gradually their satisfactory aroma and flavor, and their quality deteriorates with the passage of time.

In order to eliminate these disadvantages, the addition and blending of what is often called stabilizers into milk-containing foods is known, and attempts have been made to blend stabilizers such as chlorogenic acid, α-tocopherol and vitamin C into milk-containing foods for this purpose. However, these stabilizers are unable to stabilize milk-containing foods to a satisfactory degree.

In addition, a deterioration preventive agent that is gentle on the environment and people while also being effective in retaining the quality of milk-containing foods has not yet been reported.

SUMMARY OF THE INVENTION

It is an object of the present invention to provide a deterioration preventive agent for milk-containing foods that demonstrates superior quality retention effects on milk-containing foods while also being gentle to the environment and people. It is another object of the present invention to provide aroma and flavor in the milk-containing foods. Moreover, another object of the present invention is to provide a deterioration preventive agent for milk-containing foods that can be supplied inexpensively using a simple preparation method.

As a result of earnest research to overcome the above problems, the inventors of the present invention found that specific coumarin analogs demonstrate superior deterioration prevention effects on milk-containing foods, and as a result of conducting further studies, found that the above coumarin analogs can be supplied inexpensively using a simple preparation method, thereby leading to completion of the present invention.

Namely, the present invention relates to the following:

1) a deterioration preventive agent for milk-containing foods containing as its active ingredient a coumarin analog represented by the general formula (1) below, a glycoside of that analog, or a plant extract containing the coumarin analog or its glycoside:

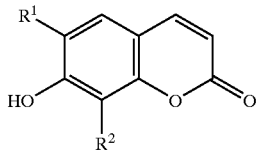

(1)

(wherein $R^1$ represents a hydrogen atom, a hydroxyl group or a methoxy group, $R^2$ represents a hydrogen atom or a hydroxyl group, and $R^1$ and $R^2$ are not both hydrogen atoms);

2) a deterioration preventive agent for milk-containing foods wherein the coumarin analog is a compound selected from esculetin, fraxetin and daphnetin;

3) a deterioration preventive agent for milk-containing foods wherein the plant extract containing a coumarin analog or its glycoside is an extract from an olive plant;

4) a deterioration preventive agent for milk-containing foods wherein the plant extract containing a coumarin analog or its glycoside is an extract from the bark or leaf of a Japanese horse chestnut tree;

5) a deterioration preventive agent for milk-containing foods wherein the plant extract containing a coumarin analog or its glycoside is an extract of a beefsteak plant;

6) a quality retention method for milk-containing foods comprising the addition of the above deterioration preventive agent for milk-containing foods to a milk-containing food; and 7) a milk-containing food containing the above deterioration preventive agent for milk-containing foods.

DESCRIPTION OF THE PREFERRED EMBODIMENTS

The following provides a detailed explanation of the present invention.

The deterioration preventive agent for milk-containing foods referred to in the present invention has as its active ingredient the coumarin analog represented by the above-mentioned general formula (1), its glycoside, or a plant extract containing the coumarin analog or its glycoside.

Particularly preferable examples of the above coumarin analog include esculetin represented by the following formula (2):

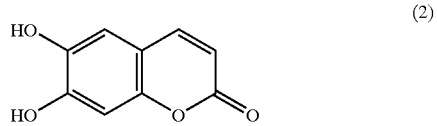

(2)

fraxetin represented by the following formula (3):

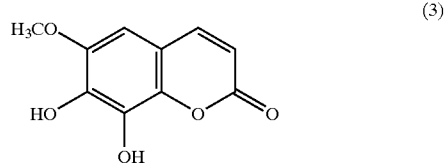

(3)

and daphnetin represented by the following formula (4):

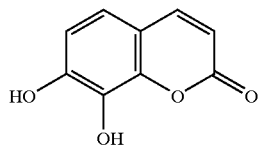

(4)

Glycosides of the above coumarin analogs are also effective as deterioration preventive agents for milk-containing foods. Examples of these glycosides include esculin, fraxetin and daphnin.

The method for preparing these glycosides is known, and is described in, for example, J. Pharm., 113 (9), 670–675, 1993 (Konishi, A., Wada, S. and Kiyosawa, O.) and J. Ethnopharmacology, 39, 205–208, 1993 (Kostova, I., Nikolov, N. and Chipinska, L. N.).

In the present invention, a plant extract containing a coumarin analog or its glycoside may also be used as a deterioration preventive agent for milk-containing foods.

These deterioration preventive agents for milk-containing foods can be prepared and acquired in accordance with ordinary methods from plants containing large amounts of coumarin analogs or their glycosides.

Specific examples of plant bodies containing large amounts of the above coumarin analogs or their glycosides that can be easily acquired include the bark and stem of ash trees (*Fraxinus*) and olive trees (*Olea*), the bark and root of Japanese horse chestnut and horse chestnut trees (*Aesculus*), the leaf and stem of beefsteak plants (*Perilla*), the leaf, flower, stem, bark or root of *Daphne* trees and *Zoisia* macrostachya trees (*Daphne*), the tuber, leaf or stem of a potato plant, the flower of *Cytisus scoparus* (*Cytisus*), the root or rootstock of Scopolia plant, or the roots and so forth of plants of the Oenanthajavanica family such as the Scopolia Rhizome (Scopolis and plants of the same species), parsley (*Petroselium*) and celery (*Apium*). In addition, examples of plants containing comparatively large amounts of the above compounds that can be used include the leaf of *Pulicaria dysenterica*, the leaf of *Haplopappus multifolius*, the above ground portion of *Gochnatica argentina*, the root of *Bupleurum fruticosum* and the above ground portion of *Pterocaulon purpurascens*.

The bark and leaf of olive trees (*Olea*), the leaf and bark of Japanese horse chestnut trees and the leaf and steam of beefsteak plant (*Perilla*) are particularly preferable examples of these plants.

The above plant raw materials may be used alone or by combining two or more types. There are no particular restrictions on the site used provided it contains a large amount of the above compounds.

These plant raw materials are dried and cut to a suitable size. Next, the plant raw materials are immersed in a solvent under fixed conditions followed by filtration and removal of plant raw materials from the solvent and concentration. Moreover, purification treatment is then performed to obtain the desired compound.

The following provides a more detailed explanation of the above procedure.

When extracting the above compounds from the plants, one type or two or more types of solvents are preferably used that are selected from water, lower alcohols, water-containing lower alcohols, polyol-based organic solvents, petroleum ether, ethyl acetate, methyl acetate, chloroform and hydrocarbons.

Here, lower alcohols refer to alcohols having 1 to 4 carbons, and methanol and ethanol, etc. are particularly preferable. In addition, water-containing lower alcohols can be used having a moisture content of 10 to 75 wt %.

Moreover, specific examples of polyol-based organic solvents include ethylene glycol and propylene glycol. Commercially available products are usually used for the petroleum ether, ethyl acetate, methyl acetate, chloroform, etc. While examples of hydrocarbon solvents include aliphatic hydrocarbons, alicyclic hydrocarbons and aromatic hydrocarbons that are a liquid at normal temperatures, aliphatic hydrocarbons and aromatic hydrocarbons that are a liquid at normal temperatures, and particularly hydrocarbons such as n-hexane (hereinafter referred to as hexane) and toluene, are preferred.

There are no particular restrictions on the extraction procedure, and although the procedure varies depending on the above plant and solvent used, extraction is usually carried out by immersing or gently stirring the plant in the above solvent at a temperature of room temperature to 80° C. Further, the use of an apparatus such as a Soxhlet extractor that was known prior to the present application allows an extract to be obtained efficiently.

The amount of time required for extraction is generally about 30 minutes to 12 hours. Furthermore, a multi-stage extraction procedure known prior to the present application may also be used.

In addition to extracts obtained according to the above methods, extracts obtained by performing some form of treatment on said extracts, such as a concentrate from which the solvent has been additionally removed from the extract, or what is called an extract in which a specific compound has been additionally removed from the extract, are also included in the extract of the present invention. For example, extracts obtained by treating the extracts with various permeable membranes are included in the extract of the present invention.

In addition, the products of crushing the leaf, branch or trunk of the above plants followed by steam distillation and extraction from the resulting distillation residue are also included in the extract of the present invention.

Next, a fraction is obtained by treating the extract by chromatography. Prior to the procedure for obtaining this fraction, the solvent within the above extract may be first removed to increase viscosity, or a solvent may be further added to lower viscosity. In this case, the fraction is usually prepared such that the amount of solvent is 0.1 to 30 parts by volume, and preferably 0.5 to 20 parts by volume, relative to 1 part by weight of extract.

The method used to obtain the fraction may be carried out in accordance with ordinary methods. For example, a method should be employed in which the above extract or pre-treated extract is poured into a chromatography column fabricated and prepared in advance, an eluent composed of a solvent is poured in, and the extract allowed to be temporarily retained in the column is allowed to flow through the column with the solvent, and the solvent that flows out of the column is divided into several portions using known means. In the case of using ordinary silica gel chromatography, the column is flushed with hexane, ethyl acetate or a mixed solvent thereof. In the case of using a mixed solvent, there are no particular restrictions on the ratio of the amounts of each solvent. While elution is usually carried out at room temperature, it may be carried out at low temperature.

Next, the solvent that flows out of the column in accordance with the above method is divided using ordinary means to obtain fractions. Each fraction or a mixture of several fractions is subjected to reduced pressure to remove the solvent and obtain a concentrate. A purification procedure using high performance liquid chromatography is then repeated to allow the obtaining of the above coumarin analog.

It should be noted that the above coumarin analog can also be obtained by freeze-drying the above concentrate, re-dissolving it in a solvent, filtering out the precipitate, re-concentrating the resulting solution and repeatedly purifying by high performance liquid chromatography.

Since such a coumarin analog mixture is effective as a deterioration preventive agent for milk-containing foods, the greater the content of coumarin analog mixture, the better the deterioration prevention capability.

The quality of milk-containing foods can be retained by adding and blending a deterioration preventive agent for milk-containing foods prepared in this manner to a milk-containing food.

There are no particular restrictions on the above milk-containing foods provided they are foods that contain milk ingredients, specific examples of which include fermented milk products (such as hard yogurt, soft yogurt, yogurt drinks and frozen yogurt), milk-containing acidic beverages (such as lactobacillus drinks having a pH of 5.0 or lower, milk drinks containing fermented milk, carbonated beverages, alcoholic beverages and fruit juice drinks), frozen confections (such as ice cream and sherbet), milk-containing desserts (such as jelly, mousse, Bavarian cream, pudding and cream), dairy products (such as butter, margarine and cheese), milk-containing confections (such as pies, candy and gum) and various other stews, potage and gratin foods.

While the amount of deterioration preventive agent blended in milk-containing foods varies depending on the kind of milk-containing foods, an amount of 0.1 ppb to 1 wt % is preferably added normally. The blending amount of 1 ppb to 0.1 wt % is more preferred.

Although the above deterioration preventive agent for milk-containing foods may be added and blended directly into the above foods, a method is normally used in which the deterioration preventive agent for milk-containing foods is preliminarily added to a solution or dispersion, after which this solution or dispersion is added and blended into the foods. Various additives such as thickeners, surfactants and antioxidants may be added in advance to this solution or dispersion.

Examples of media used to obtain the above solution or dispersion include water, ethanol glycerin and other medium chain fatty acid esters, purified vegetable oils such as coconut oil and corn oil, and edible oils.

Although the amount of the deterioration preventive agent for milk-containing foods to be added to the solvent varies considerably according to the food to which the agent is added and blended, and so forth, it is, for example, 10 ppm to 50 wt %.

The quality of milk-containing foods can be retained for a long period of time by blending the deterioration preventive agent for milk-containing foods of the present invention into milk-containing foods. Especially an extinction of aroma and flavor existed in milk-containing foods can be prevented for a long period by blending the deterioration preventive agent for milk-containing foods. Moreover, since the deterioration preventive agent for milk-containing foods can be obtained at low cost and the amount of deterioration preventive agent blended is smaller, it is economically advantageous.

EXAMPLES

The present invention will be described below in more detail by way of Examples and Comparative examples, but the present invention is not limited to these examples.

Example 1

Deterioration Preventive Agent for Milk-containing Foods Comprised of Esculetin

Commercially available esculetin was used as a deterioration preventive agent for milk-containing foods, and an ethanol solution containing 1 wt % of this deterioration preventive agent for milk-containing foods was prepared and used as a solution containing the deterioration preventive agent.

Example 2

Effect on Milk

The ability to prevent deterioration of the deterioration preventive agent for milk-containing foods of Example 1 was evaluated with the samples indicated below.

a) Preparation of Evaluation Samples

The deterioration preventive agent for milk-containing foods was added and blended into milk in the amounts described in Table 2 to prepare evaluation samples.

| | |
|---|---|
| Milk | 25% |
| Solution containing deterioration preventive agent | Various concentrations |
| Distilled water | q.s. |
| | 100% | b) Evaluation Method b-1) Evaluation Relative to Passage of Time

The above samples were heated to 85° C., filled into cans and then filled with nitrogen gas followed by sterilizing under conditions of 124° C. and 20 minutes and conducting a maltreating test under the following conditions.

Deterioration Test Conditions:

Temperature: room temperature

Duration: Allowed to stand for six months

Following completion of this test, the flavor and aroma of the samples used in the maltreating test were evaluated in the form of a sensory evaluation by 10 expert panelists. Those results are shown in Table 1.

Sensory Evaluation:

⊚: Hardly any change in flavor or aroma

○: Some change in flavor

Δ: Definite change in flavor and aroma

X: Drastic change in flavor and aroma b-2) Evaluation Relative to Heat Deterioration The above samples were heated to 85° C., filled into cans and then filled with nitrogen gas followed by sterilizing under conditions of 124° C. and 20 minutes and conducting a deterioration test under the following conditions.

Deterioration Test Conditions:

Temperature: 55° C.

Duration: Allowed to stand for four weeks

Following completion of this test, the flavor and aroma of the samples used in the maltreating test were evaluated in the form of a sensory evaluation by 10 expert panelists. Those results are shown in Table 1.

Sensory Evaluation:
⊚: Hardly any change in flavor or aroma
○: Some change in flavor
Δ: Definite change in flavor and aroma
X: Drastic change in flavor and aroma

TABLE 1

Effects on changes with passage of time

|  |  | Added concentration (ppm) | Sensory evaluation |
|---|---|---|---|
| Comparative example 1 | Additive-free | — | X |
| Comparative example 6 | Chlorogenic acid | 100<br>50 | ○<br>X |
| Example 2 | Esculetin | 1<br>0.01<br>0.001 | ⊚<br>⊚<br>○ |
| Example 8 | Fraxetin | 1<br>0.01<br>0.001 | ⊚<br>⊚<br>○ |
| Example 14 | Daphnetin | 1<br>0.01<br>0.001 | ⊚<br>⊚<br>○ |
| Example 20 | Olive extract | 1<br>0.01<br>0.001 | ⊚<br>○<br>○ |
| Example 26 | Japanese horse chestnut tree extract | 1<br>0.01<br>0.001 | ⊚<br>○<br>○ |
| Example 32 | Beefsteak plant extract | 1<br>0.01<br>0.001 | ⊚<br>○<br>○ |

In the table, the "added concentration" refers to the concentration of the deterioration preventive agent for milk-containing foods in the sample on which the maltreating test was performed (and this shall apply similarly hereinafter).

Effects on Heat Deterioration

|  |  | Added concentration (ppm) | Sensory evaluation |
|---|---|---|---|
| Comparative example 1 | Additive-free | — | X |
| Comparative example 6 | Chlorogenic acid | 100 | X |
| Example 2 | Esculetin | 1<br>0.01<br>0.001 | ⊚<br>⊚<br>○ |
| Example 8 | Fraxetin | 1<br>0.01<br>0.001 | ⊚<br>⊚<br>○ |
| Example 14 | Daphnetin | 1<br>0.01<br>0.001 | ⊚<br>⊚<br>○ |
| Example 20 | Olive extract | 1<br>0.01<br>0.001 | ⊚<br>○<br>○ |
| Example 26 | Japanese horse chestnut. tree extract | 1<br>0.01<br>0.001 | ⊚<br>○<br>○ |
| Example 32 | Beefsteak plant extract | 1<br>0.01<br>0.001 | ⊚<br>○<br>○ |

Example 3

Effect on Whole Milk Powder

The ability to prevent deterioration of the deterioration preventive agent for milk-containing foods of Example 1 was evaluated with the samples indicated below.

a) Preparation of Evaluation Samples

| Whole milk powder | 3% |
|---|---|
| Solution containing deterioration preventive agent | Various concentrations |
| Distilled water | q.s.<br>100% | b) Evaluation Method

The evaluation samples were evaluated in the same manner as in Example 2. Those results are shown in Table 2.

TABLE 2

|  |  | Added concentration (ppm) | Sensory evaluation |
|---|---|---|---|
| Effect on change with passage of time |  |  |  |
| Comparative example 2 | Additive-free | — | X |
| Comparative example 7 | Chlorogenic acid | 100<br>50 | ○<br>X |
| Example 3 | Esculetin | 1<br>0.01<br>0.001 | ⊚<br>⊚<br>○ |
| Example 9 | Fraxetin | 1<br>0.01<br>0.001 | ⊚<br>⊚<br>○ |
| Example 15 | Daphnetin | 1<br>0.01<br>0.001 | ⊚<br>⊚<br>○ |
| Example 21 | Olive extract | 1<br>0.01<br>0.001 | ⊚<br>○<br>○ |
| Example 27 | Japanese horse chestnut tree extract | 1<br>0.01<br>0.001 | ⊚<br>○<br>○ |
| Example 33 | Beefsteak plant extract | 1<br>0.01<br>0.001 | ⊚<br>○<br>○ |
| Effect on heat deterioration |  |  |  |
| Comparative example 2 | Additive-free | — | X |
| Comparative example 7 | Chlorogenic acid | 100 | X |
| Example 3 | Esculetin | 1<br>0.01<br>0.001 | ⊚<br>⊚<br>○ |
| Example 9 | Fraxetin | 1<br>0.01<br>0.001 | ⊚<br>⊚<br>○ |
| Example 15 | Daphnetin | 1<br>0.01<br>0.001 | ⊚<br>⊚<br>○ |
| Example 21 | Olive extract | 1<br>0.01<br>0.001 | ⊚<br>○<br>○ |
| Example 27 | Japanese horse chestnut tree extract | 1<br>0.01<br>0.001 | ⊚<br>○<br>○ |
| Example 33 | Beefsteak plant extract | 1<br>0.01<br>0.001 | ⊚<br>○<br>○ |

Example 4

Effect on Sweetened Condensed Milk

The ability to prevent deterioration of the deterioration preventive agent for milk-containing foods of Example 1 was evaluated under the following conditions.

a) Preparation of Evaluation Samples

| | |
|---|---|
| Sweetened condensed milk | 7% |
| Skimmed milk powder | 3% |
| Emulsifying agent | 0.05% |
| Solution containing deterioration preventive agent | Various concentrations |
| Distilled water | q.s. 100% | b) Evaluation Method

The evaluation samples were evaluated in the same manner as in Example 2. Those results are shown in Table 3.

TABLE 3

| | | Added concentration (ppm) | Sensory evaluation |
|---|---|---|---|
| *Effect on change with passage of time* | | | |
| Comparative example 3 | Additive-free | — | X |
| Comparative example 8 | Chlorogenic acid | 100 | ◯ |
| | | 50 | X |
| Example 4 | Esculetin | 1 | ⊚ |
| | | 0.01 | ⊚ |
| | | 0.001 | ◯ |
| Example 10 | Fraxetin | 1 | ⊚ |
| | | 0.01 | ⊚ |
| | | 0.001 | ◯ |
| Example 16 | Daphnetin | 1 | ⊚ |
| | | 0.01 | ⊚ |
| | | 0.001 | ◯ |
| Example 22 | Olive extract | 1 | ⊚ |
| | | 0.01 | ◯ |
| | | 0.001 | ◯ |
| Example 28 | Japanese horse chestnut tree extract | 1 | ⊚ |
| | | 0.01 | ◯ |
| | | 0.001 | ◯ |
| Example 34 | Beefsteak plant extract | 1 | ⊚ |
| | | 0.01 | ◯ |
| | | 0.001 | ◯ |
| *Effect on heat deterioration* | | | |
| Comparative example 3 | Additive-free | — | X |
| Comparative example 8 | Chlorogenic acid | 100 | X |
| Example 4 | Esculetin | 1 | ⊚ |
| | | 0.01 | ⊚ |
| | | 0.001 | ◯ |
| Example 10 | Fraxetin | 1 | ⊚ |
| | | 0.01 | ⊚ |
| | | 0.001 | ◯ |
| Example 16 | Daphnetin | 1 | ⊚ |
| | | 0.01 | ⊚ |
| | | 0.001 | ◯ |
| Example 22 | Olive extract | 1 | ⊚ |
| | | 0.01 | ◯ |
| | | 0.001 | ◯ |
| Example 28 | Japanese horse chestnut tree extract | 1 | ⊚ |
| | | 0.01 | ◯ |
| | | 0.001 | ◯ |
| Example 34 | Beefsteak plant extract | 1 | ⊚ |
| | | 0.01 | ◯ |
| | | 0.001 | ◯ |

Example 5

Effect on Cream

The ability to prevent deterioration of the deterioration preventive agent for milk-containing foods of Example 1 was evaluated under the following conditions.

a) Preparation of Evaluation Samples

| | |
|---|---|
| Cream | 2% |
| Skimmed milk powder | 3% |
| Emulsifying agent | 0.05% |
| Solution containing deterioration preventive agent | Various concentrations |
| Distilled water | q.s. 100% | b) Evaluation Method

The evaluation samples were evaluated in the same manner as in Example 2. Those results are shown in Table 4.

TABLE 4

| | | Added concentration (ppm) | Sensory evaluation |
|---|---|---|---|
| *Effect on change with passage of time* | | | |
| Comparative example 4 | Additive-free | — | X |
| Comparative example 9 | Chlorogenic acid | 100 | ◯ |
| | | 50 | X |
| Example 5 | Esculetin | 1 | ⊚ |
| | | 0.01 | ⊚ |
| | | 0.001 | ◯ |
| Example 11 | Fraxetin | 1 | ⊚ |
| | | 0.01 | ⊚ |
| | | 0.001 | ◯ |
| Example 17 | Daphnetin | 1 | ⊚ |
| | | 0.01 | ⊚ |
| | | 0.001 | ◯ |
| Example 23 | Olive extract | 1 | ⊚ |
| | | 0.01 | ◯ |
| | | 0.001 | ◯ |
| Example 29 | Japanese horse chestnut tree extract | 1 | ⊚ |
| | | 0.01 | ◯ |
| | | 0.001 | ◯ |
| Example 35 | Beefsteak plant extract | 1 | ⊚ |
| | | 0.01 | ◯ |
| | | 0.001 | ◯ |
| *Effect on heat deterioration* | | | |
| Comparative example 4 | Additive-free | — | X |
| Comparative example 9 | Chlorogenic acid | 100 | X |
| Example 5 | Esculetin | 1 | ⊚ |
| | | 0.01 | ⊚ |
| | | 0.001 | ◯ |
| Example 11 | Fraxetin | 1 | ⊚ |
| | | 0.01 | ⊚ |
| | | 0.001 | ◯ |
| Example 17 | Daphnetin | 1 | ⊚ |
| | | 0.01 | ⊚ |
| | | 0.001 | ◯ |
| Example 23 | Olive extract | 1 | ⊚ |
| | | 0.01 | ◯ |
| | | 0.001 | ◯ |
| Example 29 | Japanese horse chestnut tree extract | 1 | ⊚ |
| | | 0.01 | ◯ |
| | | 0.001 | ◯ |
| Example 35 | Beefsteak plant extract | 1 | ⊚ |
| | | 0.01 | ◯ |
| | | 0.001 | ◯ |

Example 6

Effect on Fermented Milk

The ability to prevent deterioration of the deterioration preventive agent for milk-containing foods of Example 1 was evaluated under the following conditions.

a) Preparation of Evaluation Samples

| | |
|---|---|
| Commercially available plain yogurt | 93% |
| Solution containing deterioration preventive agent | Various concentrations |
| White superior soft sugar | q.s. 100% | b) Evaluation Method
b-1) Evaluation relative to change in passage of time
A maltreating test was conducted for the above samples under the following conditions.
Deterioration Test Conditions:
  Temperature: 10° C.
  Duration: Allowed to stand for 4 weeks
Following completion of this test, the flavor and aroma of the samples used in the maltreating test were evaluated in the same manner of a sensory evaluation as in Example 2. Those results are shown in Table 5.

TABLE 5

| | | Added concentration (ppm) | Sensory evaluation |
|---|---|---|---|
| Comparative example 5 | Additive-free | — | X |
| Comparative example 10 | Chlorogenic acid | 100 | Δ |
| Example 6 | Esculetin | 1 | ⊙ |
| | | 0.01 | ⊙ |
| | | 0.001 | ○ |
| Example 12 | Fraxetin | 1 | ⊙ |
| | | 0.01 | ⊙ |
| | | 0.001 | ○ |
| Example 18 | Daphnetin | 1 | ⊙ |
| | | 0.01 | ⊙ |
| | | 0.001 | ○ |
| Example 24 | Olive extract | 1 | ⊙ |
| | | 0.01 | ○ |
| | | 0.001 | ○ |
| Example 30 | Japanese horse chestnut tree extract | 1 | ⊙ |
| | | 0.01 | ○ |
| | | 0.001 | ○ |
| Example 36 | Beefsteak plant extract | 1 | ⊙ |
| | | 0.01 | ○ |
| | | 0.001 | ○ |

Example 7

Deterioration Preventive Agent for Milk-containing Foods Comprised of Fraxetin

Commercially available fraxetin was used as a deterioration preventive agent for milk-containing foods, and an ethanol solution containing 1 wt % of this deterioration preventive agent for milk-containing foods was prepared to obtain a solution containing the deterioration preventive agent.

Examples 8 to 12

Evaluation samples containing the deterioration preventive agent for milk-containing foods of Example 7 were prepared according to the same procedure as Examples 2 to 6. Next, evaluation samples were prepared were prepared according to the same methods as Examples 2 and 6. Those results are shown in Tables 1 through 5.

Example 13

Deterioration Preventive Agent for Milk-containing Foods Comprised of Daphnetin

Commercially available daphnetin was used as a deterioration preventive agent for milk-containing foods, and an ethanol solution containing 1 wt % of this deterioration preventive agent for milk-containing foods was prepared to obtain a solution containing the deterioration preventive agent.

Examples 14 to 18

Evaluation samples containing the deterioration preventive agent for milk-containing foods of Example 13 were prepared according to the same procedure as Examples 2 to 6. Next, evaluation samples were evaluated according to the same methods as Examples 2 and 6. Those results are shown in Tables 1 through 5.

Example 19

Preparation of Deterioration Preventive Agent for Milk-containing Foods Derived from Olive Extract 100 g of dried olive leaves were crushed with a mill and placed in a Soxhlet extractor followed by the addition of 1,000 ml of 50% hydrous ethanol and extracting for 8 hours at room temperature. A concentrate of the extract was distributed at room temperature with 2,000 ml of water-hexane mixed solvent (water:hexane=1:1 ratio by volume). The above mixed solvent was left to stand overnight at 5° C. followed by obtaining the aqueous fraction. The aqueous fraction was concentrated and dried to a solid by freeze-drying to obtain a deterioration preventive agent for milk-containing foods.

The yield was 18.0 wt % (relative to the dried olive leaves).

An ethanol solution containing 1 wt % of this deterioration preventive agent for milk-containing foods was prepared and used as a solution containing deterioration preventive agent.

Examples 20 to 24

Evaluation samples containing the deterioration preventive agent for milk-containing foods of Example 19 were prepared according to the same procedure as Examples 2 to 6. Next, evaluation samples were prepared according to the same methods as Examples 2 and 6. Those results are shown in Tables 1 through 5.

Example 25

Preparation of Deterioration Preventive Agent for Milk-containing Foods Derived from Japanese Horse Chestnut Bark Extract A deterioration preventive agent for milk-containing foods was obtained by carrying out the same procedure as Example 19 with the exception of using dried Japanese horse chestnut bark and leaves instead of dried olive leaves. The yield was 15.6 wt % (relative to the dried Japanese horse chestnut bark and leaves). An ethanol solution containing 1 wt % of this deterioration preventive agent for milk-containing foods was prepared and used as a solution containing the deterioration preventive agent.

Examples 26 to 30

Evaluation samples containing the deterioration preventive agent for milk-containing foods of Example 25 were prepared according to the same procedure as Examples 2 to 6. Next, evaluation samples were prepared according to the same methods as Examples 2 and 6. Those results are shown in Tables 1 through 5.

Example 31

**Preparation of Deterioration Preventive Agent for Milk-containing Foods Derived from Beefsteak Plant (*Perilla*) Extract**

A deterioration preventive agent for milk-containing foods was obtained by carrying out the same procedure as Example 19 with the exception of using dried beefsteak plant leaves and stems instead of dried olive leaves. The yield was 15.9 wt % (relative to the dried beefsteak plant leaves and stems).

An ethanol solution containing 1 wt % of this deterioration preventive agent for milk-containing foods was prepared and used as a solution containing the deterioration preventive agent.

Examples 32 to 36

Evaluation samples containing the deterioration preventive agent for milk-containing foods of Example 31 were prepared according to the same procedure as Examples 2 to 6. Next, evaluation samples were prepared according to the same methods as Examples 2 and 6. Those results are shown in Tables 1 through 5.

Comparative Examples 1 to 5 Control

Samples were prepared by carrying out the same procedure as Examples 2 to 6 with the exception of not containing a deterioration preventive agent for milk-containing foods. These samples were evaluated by sensory evaluation under the sample conditions as Examples 2 and 6. The results obtained are shown in Tables 1 through 5.

Comparative Examples 6 to 10 Chlorogenic Acid

Samples were prepared by carrying out the same procedure as Examples 2 to 6 with the exception of using chlorogenic acid instead of the deterioration preventive agent for milk-containing foods of Examples 2 to 6. These samples were evaluated by sensory evaluation under the sample conditions as Examples 2 and 6. The results obtained are shown in Tables 1 through 5.

What is claimed is:

1. A deterioration preventive agent for milk-containing foods containing as its active ingredient a coumarin analog represented by the general formula (1) below, a glycoside of the analog, or a plant extract containing the coumarin analog or its glycoside:

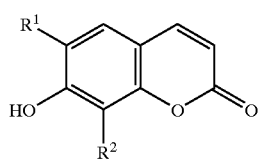

(1)

wherein $R^1$ represents a hydrogen atom, a hydroxyl group or a methoxy group, $R^2$ represents a hydrogen atom or a hydroxyl group, and $R^1$ and $R^2$ are not both hydrogen atoms.

2. The deterioration preventive agent for milk-containing foods according to claim 1, wherein the coumarin analog is a compound selected from esculetin, fraxetin and daphnetin.

3. The deterioration preventive agent for milk-containing foods according to claim 1, wherein the plant extract containing a coumarin analog or its glycoside is an extract from an olive plant.

4. The deterioration preventive agent for milk-containing foods according to claim 1, wherein the plant extract containing a coumarin analog or its glycoside is an extract from the bark or leaf of a Japanese horse chestnut tree.

5. The deterioration preventive agent for milk-containing foods according to claim 1, wherein the plant extract containing a coumarin analog or its glycoside is an extract of a beefsteak plant.

6. A quality retention method for milk-containing foods comprising the addition of at least one of the deterioration preventive agents for milk-containing foods as set forth in claim 1 to a milk-containing food.

7. A milk-containing food containing at least one of the deterioration preventive agents for milk-containing foods as set forth in claim 1.

8. A quality retention method for milk-containing foods comprising the addition of at least one of the deterioration preventive agents for milk-containing foods as set forth in claim 2 to a milk-containing food.

9. A quality retention method for milk-containing foods comprising the addition of at least one of the deterioration preventive agents for milk-containing foods as set forth in claim 3 to a milk-containing food.

10. A quality retention method for milk-containing foods comprising the addition of at least one of the deterioration preventive agents for milk-containing foods as set forth in claim 4 to a milk-containing food.

11. A quality retention method for milk-containing foods comprising the addition of at least one of the deterioration preventive agents for milk-containing foods as set forth in claim 5 to a milk-containing food.

12. A milk-containing food containing at least one of the deterioration preventive agents for milk-containing foods as set forth in claim 2.

13. A milk-containing food containing at least one of the deterioration preventive agents for milk-containing foods as set forth in claim 3.

14. A milk-containing food containing at least one of the deterioration preventive agents for milk-containing foods as set forth in claim 4.

15. A milk-containing food containing at least one of the deterioration preventive agents for milk-containing foods as set forth in claim 5.

* * * * *